United States Patent [19]

Coppel et al.

[11] Patent Number: 5,457,029
[45] Date of Patent: Oct. 10, 1995

[54] NUCLEAR ANTIGEN LA

[75] Inventors: Ross L. Coppel, Armadale; Allan D. Sturgess, North Melbourne, both of Australia

[73] Assignee: Amrad Corporation Limited, Victoria, Australia

[21] Appl. No.: 331,522

[22] PCT Filed: Jun. 3, 1988

[86] PCT No.: PCT/AU88/00177

§ 371 Date: Mar. 29, 1989

§ 102(e) Date: Mar. 29, 1989

[87] PCT Pub. No.: WO88/09932

PCT Pub. Date: Dec. 15, 1988

[30] Foreign Application Priority Data

Jun. 3, 1987 [AU] Australia .............................. PI2285/87

[51] Int. Cl.⁶ ...................... G01N 33/543; G01N 33/564
[52] U.S. Cl. ...................... 435/7.95; 435/69.3; 435/69.7; 435/975; 436/508; 436/518; 436/543
[58] Field of Search .............................. 435/7, 810, 69.3, 435/69.7, 7.95, 975; 436/508, 518, 543; 935/12, 47

[56] References Cited

U.S. PATENT DOCUMENTS 4,751,181  6/1988  Keene ..................................... 436/506

OTHER PUBLICATIONS

Chambers et al, *Proc. Natl. Acad. Sci. USA*, 82, 2115–2119, 1985.
Chambers et al, *Jour. Biol. Chem.* 263, 18043–18051, 1988.
Maggio, *Enzyme–Immunoassay*, CRC Press Inc., Boca Raton, Fla., 1980, pp. 39 and 181–192.
St Clair et al, *Arth. Rheum.*, 30, (4), 534, 1987.
St Clair et al, *Arth. Rheum.*, 31, 506–514, 1988.
Vi Mehra et al, *Proc. Natl. Acad. Sci. USA*, 83, 7013–7017, 1986.

Primary Examiner—David Saunders
Attorney, Agent, or Firm—Scully, Scott, Murphy & Presser

[57] ABSTRACT

A diagnostic test for detection of antinuclear antibody anti-La in a serum sample, comprises contacting the serum sample with a support having immobilised thereon a synthetic polypeptide displaying the antigenicity of all or a portion of the human autoantigen La, or an antigenically active fragment thereof, and detecting the presence of anti-La antibody bound to the synthetic polypeptide or fragment.

6 Claims, 4 Drawing Sheets

```
GluPheAsnArgLeuAsnArgLeuThrThrAspPheAsnValIl
GAATTCAACAGGTTGAACCGTCTAACAACAGACTTTAATGTAAT
     10        20        30        40
IleSerGluAspLysThrLysIleArgArgSerProSerLysPr
ATCAGTGAAGATAAAACTAAAATCAGAAGGTCTCCAAGCAAACC
     94       104       114       124
AsnArgSerValTyrIleLysGlyPheProThrAspAlaThrLe
AACAGATCTGTTTATATTAAAGGCTTCCCAACTGATGCAACTCT
    178       188       198       208
LeuAsnIleGlnMetArgArgThrLeuHisLysAlaPheLysGl
CTAAATATTCAGATGAGAAGAACATTGCATAAAGCATTTAAGGG
    262       272       282       292
LysPheValGluThrProGlyGlnLysTyrLysGluThrAspLe
AAATTTGTAGAGACCCCTGGCCAGAAGTACAAAGAAACAGACCT
    346       356       366       376
GluGluArgLysGlnAsnLysValGluAlaLysLeuArgAlaLy
GAAGAAAGAAAACAAAATAAAGTGGAAGCTAAATTAAGAGCTAA
    430       440       450       460
GluMetLysSerLeuGluGluLysIleGlyCysLeuLeuLysPh
GAAATGAAATCTCTAGAAGAAAAGATTGGATGCTTGCTGAAATT
    514       524       534       544
HisIleLeuPheSerAsnHisGlyGluIleLysTrpIleAspPh
CACATACTTTTCTCAAATCATGGTGAAATAAAATGGATAGACTT
    598       608       618       628
LysAlaLysGluAlaLeuGlyLysAlaLysValAlaAsnAsnGl
AAAGCCAAGGAAGCATTGGGTAAAGCCAAAGTTGCAAATAATGG
    682       692       702       712
LeuGluGlyGluValGluLysGluAlaLeuLysLysIleIleGl
CTAGAAGGAGAGGTGGAAAAAGAAGCACTGAAGAAAATAATAGA
    766       776       786       796
ArgArgPheLysGlyLysGlyLysGlyAsnLysAlaAlaGlnPr
CGTAGATTTAAAGGAAAAGGAAAGGGTAATAAAGCTGCCCAGCC
    850       860       870       880
ThrLysPheAlaSerAspAspGluHisAspGluHisAspGluAs
ACGAAATTTGCTAGTGATGATGAACATGATGAACATGATGAAAA
    934       944       954       964
AspLysGluGluProAlaSerLysGlnGlnLysThrGluAsnGl
GACAAAGAAGAACCTGCATCCAAACAACAGAAAACAGAAAATGG
   1018      1028      1038      1048
TTTTAATAGGTTTTAACGACTTTTGTTTGCGGGGCTTTTAAAAG
   1102      1112      1122      1132
AGGAAAATTTTT
   1186
```

*Fig. 1a.*

```
eValGluAlaLeuSerLysSerLysAlaGluLeuMetGlu
TGTGGAAGCATTGAGCAAATCCAAGGCAGAACTCATGGAA
     50        60        70        80
oLeuProGluValThrAspGluTyrLysAsnAspValLys
CCTACCTGAAGTGACTGATGAGTATAAAAATGATGTAAAA
    134       144       154       164
uAspAspIleLysGluTrpLeuGluAspLysGlyGlnVal
TGATGACATAAAAGAATGGTTAGAAGATAAAGGTCAAGTA
    218       228       238       248
ySerIlePheValValPheAspSerIleGluSerAlaLys
ATCAATTTTGTTGTGTTTGATAGCATTGAATCTGCTAAG
    302       312       322       332
uLeuIleLeuPheLysAspAspTyrPheAlaLysLysAsn
GCTAATACTTTTCAAGGACGATTACTTTGCCAAAAAAAT
    386       396       406       416
sGlnGluGlnGluAlaLysGlnLysLeuGluGluAspAla
ACAGGAGCAAGAAGCAAAACAAAAGTTAGAAGAAGATGCT
    470       480       490       500
eSerGlyAspLeuAspAspGlnThrCysArgGluAspLeu
TTCGGGTGATTTAGATGATCAGACCTGTAGAGAAGATTTA
    554       564       574       584
eValArgGlyAlaLysGluGlyIleIleLeuPheLysGlu
CGTCAGAGGAGCAAAAGAGGGGATAATTCTATTTAAAGAA
    638       648       658       668
yAsnLeuGlnLeuArgAsnLysGluValThrTrpGluVal
TAACCTACAATTAAGGAACAAAGAAGTGACTTGGGAAGTA
    722       732       742       752
uAspGlnGlnGluSerLeuAsnLysTrpLysSerLysGly
AGACCAACAAGAATCCCTAAACAAATGGAAGTCAAAAGGT
    806       816       826       836
oGlySerGlyLysGlyLysValGlnPheGlnGlyLysLys
TGGGTCTGGTAAAGGAAAAGTACAGTTTCAGGGCAAGAAA
    890       900       910       920
nGlyAlaThrGlyProValLysArgAlaArgGluGluThr
TGGTGCAACTGGACCTGTGAAAAGAGCAAGAGAAGAAACA
    974       984       994      1004
yAlaGlyAspGln***
TGCTGGAGACCAGTAGTTTAGTAAACCAATTTTTTATTCA
   1058      1068      1078      1088
GAAAACCGAATTAGGTCCACTTCATGTCCACCTGTGAGAA
   1142      1152      1162      1172
```

NUCLEAR ANTIGEN LA

This invention relates to nuclear antigens, in particular the human autoantigen La, and to the use of a synthetic polypeptide displaying the antigenicity of the human autoantigen La, antigenic fragments thereof or fused polypeptides containing the antigenic polypeptide or fragments in diagnostic tests for the detection of the antinuclear antibody, anti La, in serum.

Autoantibodies reactive with nuclear antigens characterise many human autoimmune diseases (1). The antinuclear antibody (ANA) anti La is very strongly associated with Sjögrens Syndrome, one of the multisystem rheumatic diseases, and serves as a diagnostic marker of that disease (2). The nuclear antigen La, with which anti La reacts, has been extensively studied to determine its nature and possible relationship to the etiology of Sjögrens Syndrome, and, as reported by several groups, La is a protein of MW 48-50kD which associates with a series of small nuclear RNAs (3).

It will be appreciated that polypeptides displaying antigenicity characteristics of the human autoantigen La are of particular utility in highly specific and sensitive diagnostic immunoassays, such as an ELISA for the detection of the antinuclear antibody (ANA), anti-La.

Sensitive immunoassays have previously only been available for the detection of antibodies to autoantigens that are abundant in cells and which can be readily purified biochemically (5,6,7). Biochemical purification of extractable nuclear antigens (ENA) results in extremely small yields of pure autoantigen (8). While the source of tissue for the biochemical purification of La has been bovine or rabbit thymus (9,10,11,12,13), differences have been demonstrated between La from human, bovine and murine tissue (14,15) suggesting that La of human origin would be the preferred source of autoantigen for diagnostic assays.

In accordance with the present invention, there is provided a diagnostic test for the detection of the antinuclear antibody anti-La in a serum sample, which comprises the steps of:

(a) contacting the serum sample with a support having immobilised thereon a synthetic polypeptide displaying the antigenicity of all or a portion of the human autoantigen La or an antigenically active fragment thereof, the amino acid sequence of said polypeptide or fragment comprising or including the sequence
LeuGluGlyGluValGluLysGluAlaLeuLysLysIleIle GluAspGlnGlnGluSerLeuAsnLysTrpLysSerLysGly ArgArgPheLysGlyLysGlyLysGlyAsnLysAlaAlaGln ProGlySerGlyLysGlyLysValGlnPheGlnGlyLysLys
ThrLysPheAlaSerAspAspGluHisAspGluHisAspGlu AsnGlyAlaThrGlyProValLysArgAlaArgGluGluThr AspLysGluGluProAlaSerLysGlnGlnLysThrGluAsn GlyAlaGlyAspGln or an epitope thereof; and (b) detecting the presence of anti-La antibody in said serum bound to said synthetic polypeptide or fragment.

This invention also provides a diagnostic test kit for detection of antinuclear antibody anti-La in a serum sample, which comprises:

(a) a support having immobilised thereon a synthetic polypeptide displaying the antigenicity of all or a portion of the human autoantigen La or an antigenically active fragment thereof, the amino acid sequence of said polypeptide or fragment comprising or including the sequence
LeuGluGlyGluValGluLysGluAlaLeuLysLysIleIle GluAspGlnGlnGluSerLeuAsnLysTrpLysSerLysGly ArgArgPheLysGlyLysGlyLysGlyAsnLysAlaAlaGln ProGlySerGlyLysGlyLysValGlnPheGlnGlyLysLys
ThrLysPheAlaSerAspAspGluHisAspGluHisAspGlu AsnGlyAlaThrGlyProValLysArgAlaArgGluGluThr AspLysGluGluProAlaSerLysGlnGlnLysThrGluAsn GlyAlaGlyAspGln or an epitope thereof; and (b) means for detecting the presence of anti-La antibody in said serum bound to said synthetic polypeptide or fragment.

A partial cDNA sequence encoding the putative carboxyl-terminal 12% of the human La protein has been published (4), with the prediction that this 55 amino acid region contains an antigenic determinant. Following further investigations in this regard, including the use of probes derived from the published sequence to isolate homologous human cDNA clones which have been used to express portions of the La protein and to map regions of antibody reactivity, significant anomalies have now been shown to exist in the previously published sequence.

Figure 1A:
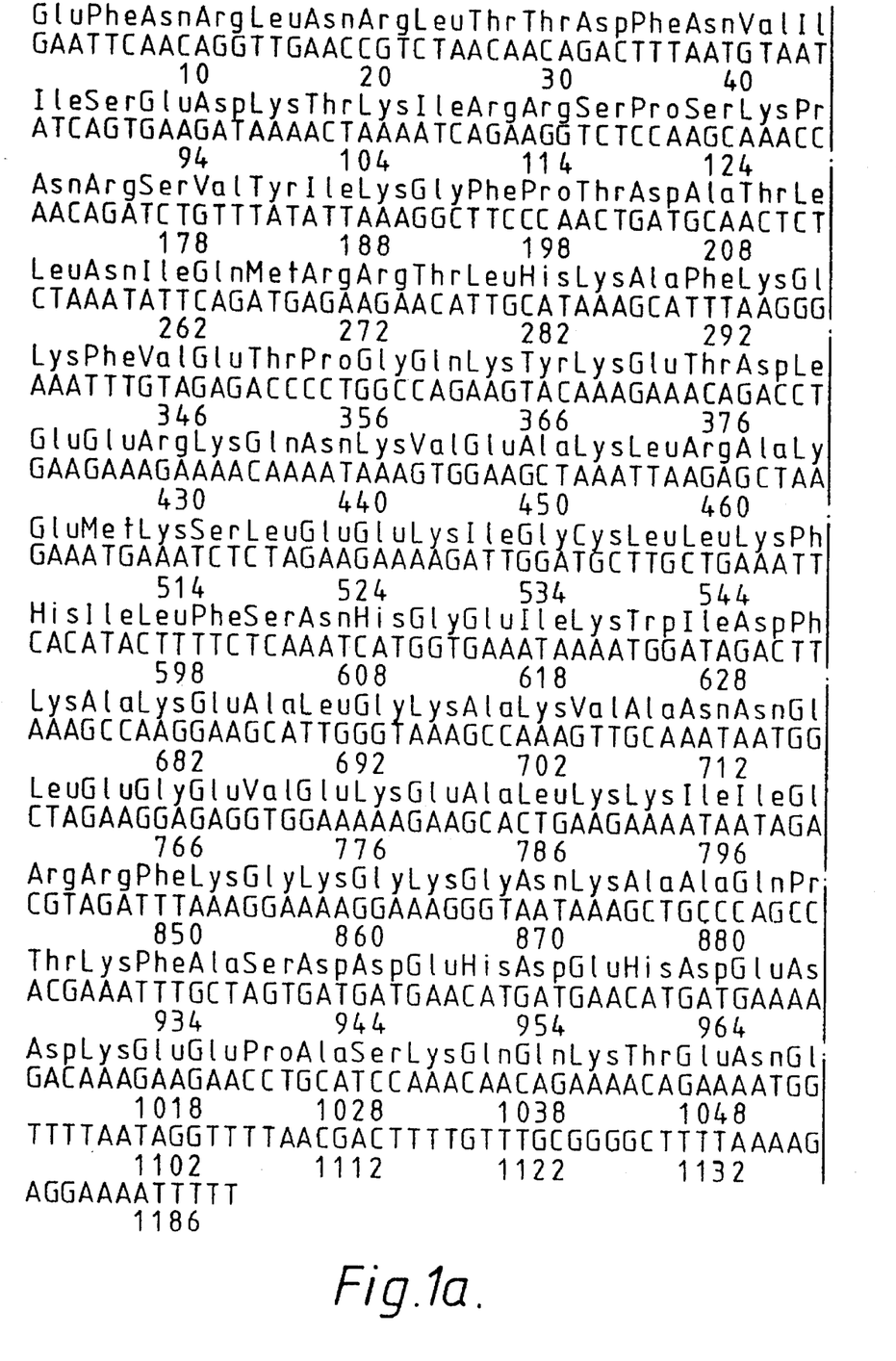
FIGS. 1a–1b show the nucleotide sequence of the cDNA of a clone encoding La, together-with the amino acid sequence for which it codes.
Figure 1B:
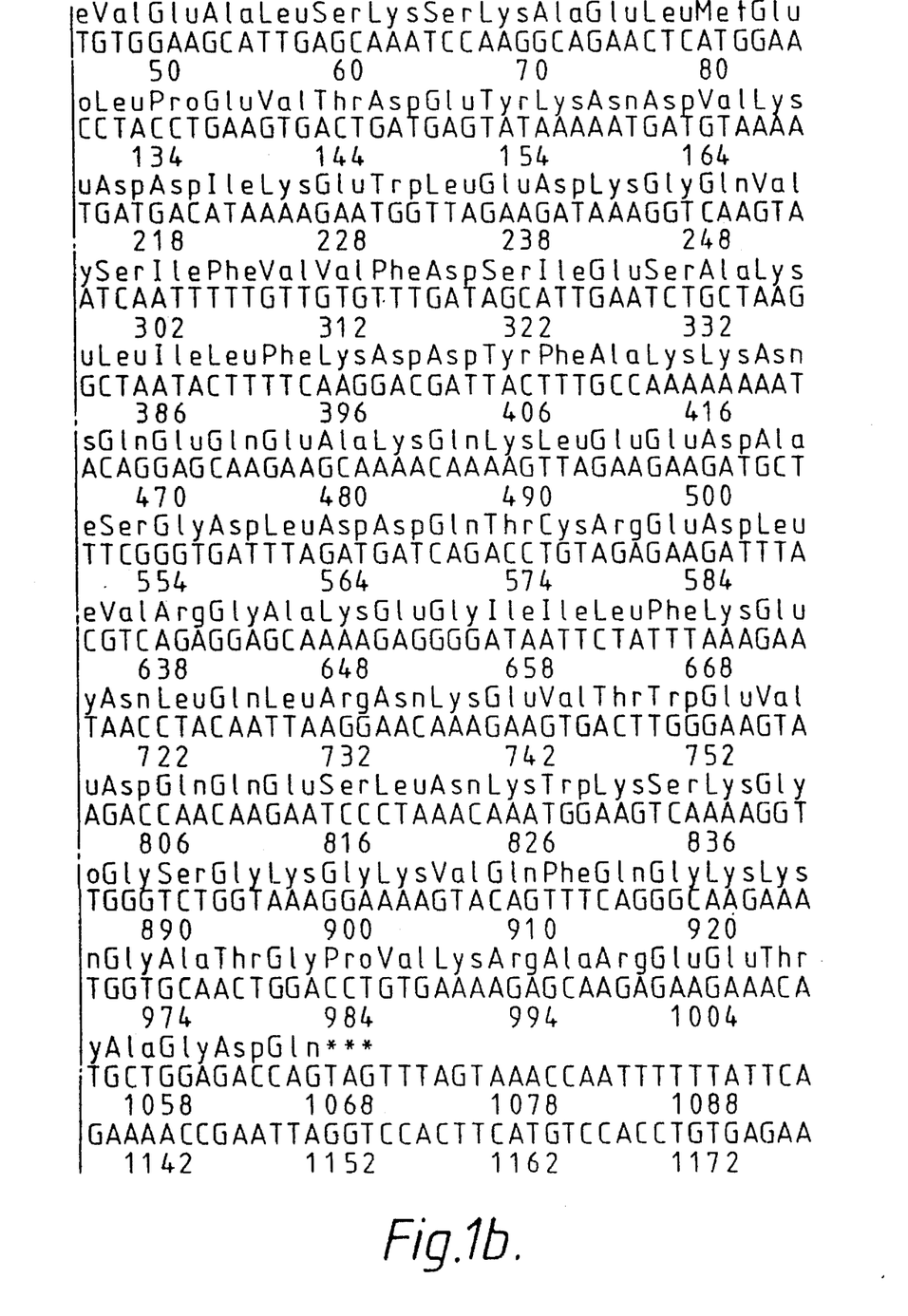

In work leading to the present invention, a recombinant DNA molecule has been constructed comprising a nucleotide sequence including all or a portion of the base sequence shown in FIGS. 1a–1b. As described in greater detail below, the nucleotide sequence of FIG. 1 is present in a La cDNA clone of 1.4kb, contains an open reading frame of 1,065kb, and encodes a polypeptide of 355 amino acids (which is estimated to be 70–80% of the full length human protein). This work has further revealed that at least one epitope of La is contained in the carboxy-terminal 103 amino acids of the sequence as set out in FIGS. 1a–1b.

This work has enabled the production of fused polypeptides comprising polypeptide sequences displaying the antigenicity of the human autoantigen La as the C-terminal sequence, and an additional peptide or polypeptide, for example a polypeptide coded for by the DNA of a cloning vehicle, as the N-terminal sequence fused thereto. Such fused polypeptides can be produced by host cells transformed or infected with a recombinant DNA cloning vehicle comprising an expression control sequence having promoter sequences and initiator sequences, and a nucleotide sequence capable of being expressed as a polypeptide displaying the antigenicity of the human autoantigen La. The fused polypeptide can be subsequently isolated from the host cell to provide the fused polypeptide substantially free of other host cell proteins. If desired, the fused polypeptide may be cleaved to remove the fused N-terminal sequence.

The present invention involves the use of synthetic peptides or polypeptides displaying the antigenicity of the human autoantigen La. As used herein, the term "synthetic" means that the peptides or polypeptides have been produced by chemical or biological means, such as by means of chemical synthesis or by recombinant DNA techniques leading to biological synthesis. Such polypeptides can, of course, be obtained by cleavage of a fused polypeptide as described above and separation of the desired polypeptide from the additional polypeptide coded for by the DNA of the cloning vehicle by methods well known in the art. Alternatively, once the amino acid sequence of the desired polypeptide has been established, for example, by determination of the nucleotide sequence coding for the desired polypeptide, the polypeptide may be produced synthetically, for example by the well-known Merrifield solid-phase synthesis procedure.

Further features of the present invention will be apparent from the detailed description in the following Examples, which are included by way of illustration of the invention.

EXAMPLE 1

This Example describes the identification and characterisation of a human cDNA clone encoding La. In the drawings.

MATERIALS AND METHODS

Identification of homologous cDNA clones with an oligonucleotide probe

A cDNA library was constructed in a λgt10 using mRNA from a B cell tumor JOY (16) as described by Hariharan (17). A 37mer oligonucleotide probe was synthesised on an Applied Biosystems Model 380A Synthesizer. The sequence corresponded to nucleotides 108–146 of the published clone of Chambers and Keen (4). The probe was end-labelled with $T_4$ polynucleotide kinase and $Y\ ^{32}P$ ATP for 30 min at 37° C. in 50 mM Tris HCl (pH7.4) 10 mM $MgCl_2$, 50 mM DTT, 0.1 mM ATP followed by removal of unincorporated label. Hybridisation was carried out in 25% formamide, 5×SSC (SSC is 0.15 MNacl, 15 mM sodium citrate pH7.0), 0.25% milk powder at 42° C. Washings were in 5×SSC at 65° C.

Northern Blotting and DNA Sequencing

Northern blots using mRNA from the JOY cell line and K562 were performed basically as described by Hariharan (17) using a cDNA probe extending from nucleotides 1–500 of our sequence. Control probings were performed with c-abl cDNA.

DNA sequencing was performed by the chain termination method in M13 vectors, with Klenow and $\gamma P^{32}$ dATP (18). The sequence was analysed using the computer programs of Staden (19).

Expression Systems and Epitope Mapping

The pUR series of vectors (20) was used to express the entirety of the La cDNA and 3 fragments of it generated by digestion with ScaI. Bacterial lysates were subjected to SDS-polyacrylamide gel electrophoresis, electroblotted onto nitrocellulose (21), and probed with various autoimmune sera, followed by $^{125}I$-labelled protein A and autoradiography. All blockings, washings and antibody probings were performed with 5% milk powder in phosphate buffered saline (22). Serum dilutions were 1 in 200 and the Protein A-$I^{125}$ had a specific activity of 40 μCi/ml. Sera were absorbed with sonicates of various expressing clones to delete particular specificities.

Purifications of Recombinant La and its use in an ELISA

The La cDNA was subcloned into a vector (pEV)(23) in which the recombinant protein is expressed as a fusion protein only with a few amino acids from the polylinker of the vector. The recombinant La was purified by the method described to purify native La from HeLa cells (9), and used to develop an ELISA (See Example 2).

Affinity Purified Anti La Antibodies

Recombinant La was bound to CnBr activated Sepharose beads and reacted with the IgG portion of anti La containing sera. After extensive washing the bound anti La Ab was eluted with glycine HCl pH2.6 (25). Various control sera were applied to ensure specificity. The eluted, affinity purified anti La antibodies were tested using indirect immunofluorescence on HeLa cells and immunoblotting against a soluble nuclear preparation of HeLa cells (6). A murine monoclonal against La was also used to ensure-the identity of the recombinant material (26).

RESULTS

Isolation and Characteristics of Human cDNA clone Encoding La

A cDNA library constructed from the JOY cell line, a human B cell tumor line, was screened with the oligonucleotide probe and this detected approximately one hybridizing clone per 10,000 plaques. The largest of these, 1400 bases in length, was selected for further study. The sequence of this DNA (FIG. 1) reveals a single open reading frame beginning with an authentic EcoRI site and continuing for 1065 coding bases (encoding a polypeptide of 355 amino acids), followed by 200 bases of 3' noncoding sequence and a polyA tail. Northern blot analysis, using mRNA derived from 2 human cell lines, the Raji cell (an EBV infected B cell) and JOY, demonstrates that the full length La mRNA is approximately 2 kb, and that therefore the derived DNA sequence for La is deficient by 500–600 5' bases. The translation product has a predicted weight of 40.5 kD, approximately 9 kD less than maximum estimates of the MW of native La in reducing polyacrylamide gels. Analysis using the Kyte and Doolittle method revealed a relatively hydrophilic molecule, with no regions suggestive of membrane insertion.

A number of data banks were computer searched for homologies between La and previously described DNA or protein sequences, however, no homologies with published sequences were found other than at the 5' end (the La sequence of Chambers and Keene (4)). Because it has been suggested that cross reactions between microbiological antigens and self proteins could be responsible for the development of some autoantibodies (27), particular attention was paid to possible homologies between regions of La and any sequenced viral or bacterial antigens. No such homologies were found.

Comparison of sequence with previously published partial sequence

When the La sequence of FIGS. 1a–1b is compared to that of Chambers and Keene (4), anomalies are apparent. In particular, a single cytidine residue present at position 134 in the present sequence is missing from the published clone 159 of the published sequence). This leads to a false stop codon being read at position 168 of the published sequence. No such stop codon is found in the present sequence. To verify the present sequence, this region has been sequenced, in both orientations, and 2 independent clones used, one isolated from the JOY library and one from a T cell tumor library. Accordingly, there is no doubt that the present sequence interpretation is correct. The predicted molecular weight of the La molecule encoded by the present cDNA is 40.1 kD, which would be a minimum estimate not including post translational changes.

Expression Systems and ELISA

When the La cDNA is subcloned into pEV (23), immunoreactive La of MW approximately 40 kD is produced, in agreement with predicted MW from the DNA sequence. The evidence that this recombinant protein is La, comes from several experiments:— first, only sera shown by standard methods (counter immunoelectrophoresis against CDC prototype anti La or immunoblotting) to contain anti La will react with the recombinant protein; second, all standard anti La sera react with the recombinant protein; third, antibodies affinity purified on a column containing the recombinant protein display the immunofluorescent and immunoblot patterns characteristic of anti La; and fourth, a murine monoclonal directed to La reacts with the recombinant protein. Thus, there is overwhelming evidence that this cDNA encodes immunoreactive La.

Western blotting using the pEV produced La is an extremely sensitive method for the detection of anti La antibodies. Serum diluted to 1 in $10^5$ produces strong signals against recombinant La. Recombinant La has been purified from pEV containing E.coli cultures using a method derived from Stefano (8), designed to purify La from mammalian cells. This is a simple method producing approximately 25 μgm recombinant La/1 ml culture. (See Example 2).

Epitopes on the La molecule

Published data (28) from experiments using partial enzymatic digestion of native La in mammalian cell extracts, suggests that 2 regions of the La molecule can be separately recognised by anti La sera. Some patient sera react with both regions in immunoblots while others react with one or the other. The previously published partial cDNA for La (4) predicted that one epitope might be the strongly hydrophilic decapeptide from amino acids 31–40. To investigate epitopes on La, 3 fragments of the present cDNA, generated by ScaI digestion have been subcloned and expressed separately in plasmid vectors. One fragment was reactive with anti-La sera, establishing the existence of at least one epitope. Subclone LaI (bases 1–251) was subcloned into BTA224 and expressed as a stable fusion protein with β-galactosidase. This portion of the La molecule is not immunoreactive with anti La sera by colony immunoassay or Western blotting. Subclone LaII (bases 252–755) was also subcloned into BTA224 and an unstable fusion protein produced which has no detectable reactivity with human antibodies. Subclone LaIIIi (bases 756–1065) was subcloned using Bam linkers, into the pUR291 vector, and produced a stable fusion protein which is strongly immunoreactive in the colony immunoassay and in Western blots. In order to determine if the present cDNA encodes all the epitopes of native La, absorption experiments have been carried out. Anti La sera, absorbed with sonicates of E.coli expressing the recombinant La molecule, still demonstrate strong reactivity to the 50 kD La band in a Western blot using a nuclear preparation of HeLa cells.

EXAMPLE 2

This Example illustrates the expression of recombinant La in cell culture, purification of the product from the culture medium, and use of the purified product in a diagnostic assay.

In the drawings.

MATERIALS AND METHODS

Sera

Coded sera from 260 patients with various autoimmune diseases associated with antinuclear antibodies (ANA) and from 100 normal subjects were tested for anti-La by ELISA using recombinant La. The disease groups included primary Sjögren's syndrome (50 patients), secondary Sjögren's syndrome associated with rheumatoid arthritis (14 patients), rheumatoid arthritis (RA(20 patients)), systemic lupus erythematosus (SLE(50 patients)), mixed connective tissue disease (MCTD(19 patients)), scleroderma (50 patients), primary biliary cirrhosis (PBC(18 patients)) and autoimmune chronic active hepatitis (A-CAH(39 patients)). All patients except those with secondary SjöSgren's syndrome associated with rheumatoid arthritis were considered to have one disease only except one patient with primary Sjögren's syndrome who had had acute classical SLE 26 years previously (20).

Purification of cloned La

E.coli stock contained a pEV vector (23), with a 1.4 kb cDNA for La as described above was grown in liquid culture. Recombinant La production was induced by heat and the E.coli harvested by centrifugation. The bacterial pellet was suspended in Buffer 1 (10 mM Tris-HCl pH 8, 2 mM EDTA, 50 mM NaCl) with 0.2 mgs/ml lysozyme and mixed for 30 minutes at room temperature prior to addition of a final 0.2% concentration of Triton X-100. After mixing for 10 minutes an equal volume of Buffer 1 containing 10 mM $MgCl_2$, was added with 2 μg/ml DNAse (Cooper Biomedical, Malvern, Penna.) and the suspension mixed for a further 15 minutes. 5 μg/ml of the protease inhibitors, leupeptin, pepstatin A, chymostatin (Sigma, St.Louis) and 0.5 mM PMSF (Calbiochem, Calif.) were added and mixed for 5 minutes. The mixture was centrifuged at 2,000 rpm for 5 minutes and the resulting supernate centrifuged at 18,000 rpm for 30 minutes at 4° C. The recombinant La protein was then purified according to a method described by Stefano (8) for purification of native La nucleoprotein from HeLa cells. In preliminary studies all steps in the purification were monitored by Western blotting using a high titre anti-La-positive serum, and the results were compared with those obtained in the same Western blot using a nuclear-enriched extract of HeLa cells (14). The procedure resulted in the isolation of two immunoreactive polypeptides which were pooled and dialysed. The yield of protein was measured by the Lowry assay and the stability of the La preparation was assessed after storage under various conditions: at 4° C. in solution, at −70° C. in solution, after lyophilisation, and coated on to plastic microtitration plates (Flow Laboratories, Virgina, USA).

ELISA

Flat-bottomed wells of a 96 well microtitration plate were coated overnight at 4° C. with 1 μg lyophilised recombinant La in 50 μL distilled water. Uncoated sites in the wells were blocked by 100 μL 10% fetal calf serum in phosphate-buffered saline pH 7.4 (PBS) for one hour at room temperature. The plate was washed in PBS, triplicates of 50 μL sera diluted $10^{-3}$ were applied for 3 hours at room temperature and the plate was again washed. Goat anti-human globulin conjugated to alkaline phosphatase (Sigma, St.Louis, USA) was applied for 90 minutes at room temperature, followed by disodium p-nitrophenyl phosphate substrate solution (Sigma, St.Louis, USA). Chromophore development was monitored by measuring absorbance at 405 nm before and after addition of 3M NaOH using a Titertek Multiskan ELISA reader. For each assay a standard curve was constructed using 10-fold dilutions of the same high titre anti-La-positive serum. One unit of binding activity was defined as that given by the $10^{-6}$ dilution of the anti-La-positive control serum. Those sera with binding activities of <5 units at $10^{-3}$ dilution were arbitrarily defined as positive; this was based on an optical absorbance <5 standard deviations above the mean value for 50 normal subjects.

RESULTS

Figure 2A:
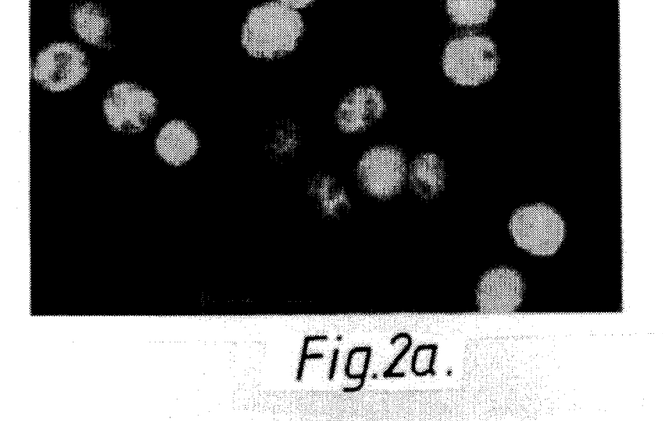
FIG. 2a shows demonstration by immunofluorescence of reactive between nuclei of HEp 2 cells and serum antibody affinity purified using recombinant La.
Figure 2B:
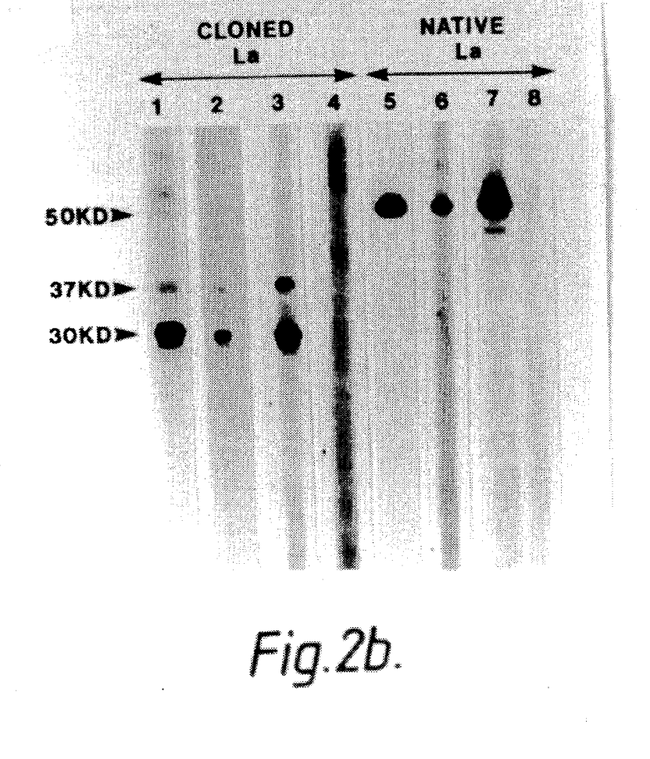
FIG. 2b shows a Western blot with cloned La and native La. Lanes 1 and 5 illustrate reactivity with affinity-purified human anti-La using recombinant La; lanes 2 and 6 reactivity with the murine monoclonal anti-La, SW5(26); lanes 3 and 7 reactivity with human anti-La; and lanes 4 and 8 non-reactivity with serum from a healthy subject.

Two polypeptides, a less abundant one of 37 kD and a major one of 30 kD, were obtained after purification of the cultures of E.coli containing the expression vector with the 1.4 kb insert of cDNA for La. The average yield of the recombinant La protein was 25 µg/ml culture. Proof that the product from E.coli was the La nucleoprotein was obtained as follows. Human anti-La that was affinity purified from recombinant La on a cyanogen bromide-activated Sepharose column (Pharmacia, Sweden) reacted with nuclei of HEp2 cells giving the characteristic La ANA pattern by immunofluorescence and also reacted with native La by Western blotting (FIG.2a and 2b); a La-specific murine monoclonal antibody, SW5, kindly provided by Dr. David Williams, Kennedy Institute, London, reacted with the recombinant La; and reactivity between human anti-La and native La was inhibited by recombinant La but not by a recombinant protein from the same strain of E.coli containing the pEV vector with a different cDNA. The preparation of recombinant La was stable for at least two months when stored in solution at 4° C. and at −70° C., after lyophilisation at −70° C., and on microtitration plates stored at 4° C.

Figure 3:
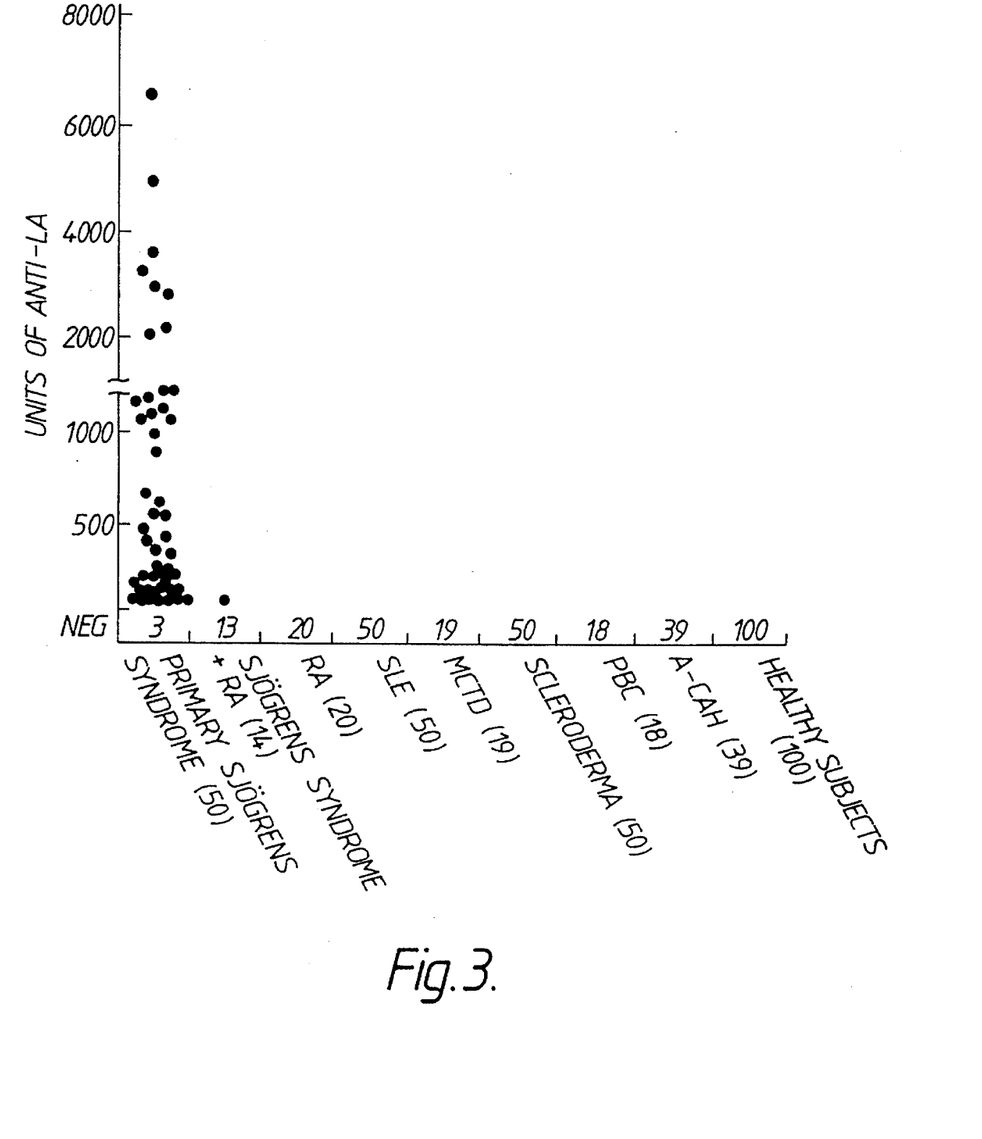
FIG. 3 shows ELISA units of anti-La in sera of patients with various autoimmune diseases and healthy subjects tested against the recombinant La nucleoprotein.

Antibodies to recombinant La protein were detected by ELISA in 47 (94%) of 50 patients with primary Sjögren's syndrome, in 1 (7%) of 14 patients with secondary Sjögren's syndrome but in none of 20 patients with RA, 50 patients with SLE, 19 patients with MCTD, 50 patients with scleroderma, 18 patients with PBC, 39 patients with A-CAH, nor in 100 healthy subjects (FIG. 3). Sera from all 48 patients who were anti-La-positive by ELISA reacted at a dilution of $10^{-3}$ or greater with both recombinant La and native La by Western blotting.

REFERENCES

1. , Tan, E.M. (1982). Autoantibodies to nuclear antigens (ANA): their immunobiology and medicine. *Adv. Immunol.* 33: 167.
2. Whittingham, S., Mackay, I.R., Tait, B.D. (1983). Autoantibodies to small nuclear ribonucleoproteins. A strong association between anti-SS-B(La), HLA-B8 and Sjögren's syndrome. *Aust. NZ. J.Med.* 13: 565.
3. Rinke, J., Steitz, J.A. (1982). Precursor molecules of both human 5S ribosomal RNA and transfer RNA are bound by a cellular protein reactive with antiLa antibodies. *Cell* 29: 149-159.
4. Chambers, J.C., Keene, J.D. (1985). Isolation and analysis of cDNA clones expressing human lupus La antigen. *Proc.Natl.Acad.Sci. USA* 82: 2115-2119.
5. Aarden, L.A., Lakmaker, F., DeGroot, E.R. Immunology of DNA. IV Quantitative aspects of the Farr assay. *J.Immunol.Meth* (1976); 11 : 153-63.
6. Fritzler, M.J., Tan, E.M. Antibodies to histones in drug-induced and idiopathic lupus erythematosus. *J. Clin. Invest.* (1978); 62 : 560-67.
7. Hardin, J.A., Thomas, J.O. Antibodies to histones in systemic lupus erythematosus Localization of prominent autoantigens on histones H1 and H2B. *Proc.Natl.Acad..Sci.* (1983); 80 : 7410-14.
2. Stefano, J.E. PUrified lupus antigen La recognizes an oligouridylate stretch common to the 3' termini of RNA polymerase III transcripts. *Cell* (1984); 36: 145-54.
9. Akizuki, M., Boehm-Truitt, M.J., Kassan, S.S., Steinberg, A.D., Chused, T.M. Purification of an acidic nuclear protein antigen and demonstration of its antibodies in subsets of patients with sicca syndrome. *J.Immunol.* (1977); 119: 932-38.
10. Teppo, A.M., Gripenberg, M. , Kurki, P., Baklien, K., Helve, T., Wegelius, 0. PUrification and characterization of a nuclear SS-B antigen. *Scand. J. Immunol.* (1982); 15: 1-7.
11. Venables, P.J.W., Charles, P.J., Buchanan, R.R.C., Yi, T., Mumford, P.A., Schrieber, L., Room, G.R.W., Maini, R.N. Quantitation and detection of isotypes of anti-SS-B antibodies by ELISA and Farr assays using affinity purified antigens. *Arthritis Rheum.* (1983); 26: 146-55.
12. Harley, J.B., Yamagata, H., Reichlin, M. Anti-La/SSB antibody is present in some normal sera and is coincident with anti-Ro/SSA precipitins in systemic lupus erythematosus. *J.Rheumatol.* (1984); 11: 309-14.
13. Maddison, P.J., Skinner, R.P., Vlachoyiannopolous, P., Brennand, DeMe Hough, D. Antibodies to nRNP, Sm, Ro(SSA) and La (SSB) detected by ELISA: their specificity and inter-relations in connective tissue disease sera. *Clin.Exp.Immunol.* (1985); 62 : 337-45.
14. McNeilage, L.J., Whittingham, S., Jack, I., Mackay, I.R. Molecular analysis of the RNA and protein components recognized by anti-La (SS-B) autoantibodies. *Clin.Exp.Immunol.* (1985); 62; 685-96.
15. Harley, J.B., Rosario, M.O., Hamagata, H., Fox, O.F., Koren, E. Immunologic and structural studies of the lupus/Sjögren's syndrome autoantigen, La/SSB, with a monoclonal antibody. *J.Clin.Invest.* (1985); 76 : 801-06.
16. Bernard, O., Cory, S., Gerondakis, S., Webb, E., Adams, J.M. (1983). *EMBO J.* 2: 2375-2383.
17. Haniharan, I.K., Adams, J.M. (1987). cDNA sequence for Human bcr, the gene that translocates to the abl oncogene in CML. *EMBO, J.* 6: 115-119.
18. Messing, J. (1983). New M13 vectors for cloning. *Methods Enzymol.* 101: 20-78.
19. Staden, R. (1982) *Nucl.Acid.Res.* 10: 4731-4751.
20. Ruther, V., Müller-Hill, B. (1985). Easy Identification of cDNA clones. *EMBO.J.* 1791-1794.
21. Towbin, H., Staehlon, T., Gordon, J. (1979). Electrophoretic transfer of proteins from polyacrylamide gels to nitrocellulose sheets: Procedure and some application. *Proc.Natl.Acad.Sci.USA* 76: 4350-4355.
22. Johnson, D.A., Gautsch, J.W., Spottsman, J.R., Elder, J.H. (1984). Improved technique utilising non-fat dry milk for analysis of proteins and nucleic acids transferred to nitrocellulose. *Gene. Anal.Tech.* 1: 3.
23. Crowl, R., Seamans, C., Lomedico, P., McAndrew, S. (1985). Versatile expression vectors for high level synthesis of cloned gene products in *E.coli. Gene* 38: 31-36.
24. Whittingham, S., Naselli,G., McNeilage, L.J., Coppel, R.L., Sturgess, A.D. (1987), Serological Diagnosis of Primary Sjögren's Syndrome Using Human Recombinant La (SS-B) as a Nuclear Antigen. *Lancet* ii, 1-3.
25. Crewther, P.E., Bianco, A.E., Brown, G.V., Coppel, R.L., Stahl, H.D., Kemp, D.J., Anders, R.F. (1986). Affinity purification of human antibodies directed against cloned antigens of *Plasmodium falciparum*. *J.Xmmunol, Methods* 86: 257.

26. Smith, P.R., Williams, D.G., Venables, P.J.W., Maini, R.N. (1985). Monoclonal antibodies to the Sjögren's syndrome associated antigen SS-B(La). *J.Immunol. Methods* 77: 63-76.
27. Walker, E.J., Jeffrey, P.D. (1986). Polymyositis and Molecular Mimicry, A mechanism of autoimmunity. *Lancet*, Sep.13 605-607.
28. Chan, E.K.L., Francoeur, A.M., Tan, E.M. (1986). Epitopes, Structural Domains, and Asymmetry of Amino Acid Residues in SS-B/La Nuclear Protein. *J.Immunol.* 136: 3744-3749.
29. Whittingham, S., McNeilage, L.J., Mackay, I.R. Epstein-Barr virus as an etiological agent in primary Sjögren's syndrome. *Medical Hypotheses* (in press).

We claim:

1. A method for the detection of antinuclear antibody anti-La in a serum sample which comprises:

(a) contacting said sample with a support having immobilized thereon a synthetic polypeptide having the amino acid sequence:
    LeuGluGlyGluValGluLysGluAlaLeuLysLysIleIle GluAspGlnGlnGluSerLeuAsnLysTrpLysSerLysGly ArgArgPheLysGlyLysGlyLysGlyAsnLysAlaAlaGln ProGlySerGlyLysGlyLysValGlnPheGlnGlyLysLys ThrLysPheAlaSerAspAspGluHisAspGluHisAspGlu AsnGlyAlaThrGlyProValLysArgAlaArgGluGluThr AspLysGluGluProAlaSerLysGlnGlnLysThrGluAsn GlyAlaGlyAspGln; and (b) detecting said anti-La antibody bound to said polypeptide.

2. The method of claim 1 wherein said polypeptide consists of a fused polypeptide produced by expression of a recombinant DNA molecule in a host cell.

3. The method of claim 1 wherein said anti-La antibody bound to said polypeptide is detected by an enzyme-linked immunosorbant assay comprising addition of an enzyme-linked anti-human globulin antiserum followed by addition of a detectable substrate for said enzyme and detection of the action on said substrate of said enzyme bound to said support.

4. A kit for detection of antinuclear antibody anti-La in a serum sample which comprises:

(a) a support having immobilized thereon a synthetic polypeptide having the amino acid sequence:
    LeuGluGlyGluValGluLysGluAlaLeuLysLysIleIle GluAspGlnGlnGluSerLeuAsnLysTrpLysSerLysGly ArgArgPheLysGlyLysGlyLysGlyAsnLysAlaAlaGln ProGlySerGlyLysGlyLysValGlnPheGlnGlyLysLys ThrLysPheAlaSerAspAspGluHisAspGluHisAspGlu AsnGlyAlaThrGlyProValLysArgAlaArgGluGluThr AspLysGluGluProAlaSerLysGlnGlnLysThrGluAsn GlyAlaGlyAspGln; and (b) means for detecting anti-La antibody bound to said polypeptide.

5. The kit of claim 4 wherein said polypeptide consists of a fused polypeptide produced by expression of a recombinant DNA molecule in a host cell.

6. The kit of claim 4 wherein said means for detecting the presence of bound anti-La antibody comprises enzyme-linked anti-human globulin antiserum and a detectable substrate for said enzyme.

* * * * *

UNITED STATES PATENT AND TRADEMARK OFFICE
CERTIFICATE OF CORRECTION

PATENT NO.   : 5,457,029
DATED        : October 10, 1995
INVENTOR(S)  : Ross L. Coppel, et al.

It is certified that error appears in the above-indentified patent and that said Letters Patent is hereby corrected as shown below:

```
        Column 3, line 1:   after "together" delete -- - --
        Column 3, line 6:   after "ensure"   delete -- - --
        Column 6, line 16:  "SjoSgren's" should read
--Sjogren's--
        Column 6, line 26:  "Recombihant" should read
--Recombinant--
        Column 6, line 33:  "Penna." should read
 --Pa--.

Column 8, line 5:   "2." should read --8.--

Column 8, line 26:  "DeMe" should read --D.M.--
        Column 8, line 65:  "J.Xmmunol" should read
--J. Immunol--

Column 9, line 27, Claim 1:  "Gin" should read
--Gln--
        Column 10, line 19, Claim 4:  "Gly" should read
--Gly--
```

Signed and Sealed this

Ninth Day of July, 1996

Attest:

*Attesting Officer*

BRUCE LEHMAN
*Commissioner of Patents and Trademarks*